United States Patent
Urbahns et al.

(10) Patent No.: US 6,495,545 B1
(45) Date of Patent: *Dec. 17, 2002

(54) 1,4-BENZODIAZEPINONE DERIVATIVES AND THEIR USE AS INTEGRIN ANTAGONISTS

(75) Inventors: Klaus Urbahns, Wuppertal (DE); Delf Schmidt, Wuppertal (DE); Ulf Brüggemeier, Leichlingen (DE); Christoph Gerdes, Leverkusen (DE); Beatrix Stelte-Ludwig, Wülfrath (DE); Jörg Keldenich, Wuppertal (DE); Elke Stahl, Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/857,981

(22) PCT Filed: Dec. 6, 1999

(86) PCT No.: PCT/EP99/09525

§ 371 (c)(1),
(2), (4) Date: Jun. 12, 2001

(87) PCT Pub. No.: WO00/35917

PCT Pub. Date: Jun. 22, 2000

Related U.S. Application Data

(62) Division of application No. 09/211,274, filed on Dec. 14, 1998.

(51) Int. Cl.$^7$ .................. C07D 413/14; C07D 417/14; A61K 31/40; A61K 31/55; A61P 19/10

(52) U.S. Cl. ............... 514/221; 540/504; 540/512; 540/513; 540/516

(58) Field of Search ................ 540/504, 512, 540/513, 516; 514/221

(56) References Cited

U.S. PATENT DOCUMENTS

| 5,403,836 A | 4/1995 | Blackburn et al. ......... 514/213 |
| 5,668,159 A | 9/1997 | Jin et al. .................... 514/363 |

FOREIGN PATENT DOCUMENTS

| WO | 9414776 | 7/1994 | ......... C07D/223/16 |
| WO | 9514683 | 6/1995 | ......... C07D/261/04 |
| WO | 9600730 | 1/1996 | ......... C07D/519/00 |
| WO | 9626190 | 8/1996 | ......... C07D/243/24 |
| WO | 9724119 | 7/1997 | ......... A61K/31/40 |

*Primary Examiner*—Bruck Kifle
(74) *Attorney, Agent, or Firm*—Jerrie L. Chiu

(57) ABSTRACT

The present invention relates to compounds of general formula (I) and their preparation and use for the production of pharmaceuticals, and pharmaceuticals comprising these compounds.

5 Claims, No Drawings

1,4-BENZODIAZEPINONE DERIVATIVES AND THEIR USE AS INTEGRIN ANTAGONISTS

This application is a divisional of Ser. No. 09/211,274, filed on Dec. 14, 1998.

The present invention relates to new multiheterocyclic compounds as integrin antagonists with a broad spectrum of action having, inter alia, antiosteoporotic, antirestenotic, anticarcinogenic and antiatherosclerotic activity. The present invention moreover relates to the preparation of these compounds and their use for the production of medicaments, and also medicaments comprising them.

Integrins are heterodimeric transmembrane proteins found on the surface of cells, which play an important part in the adhesion of the cells to an extracellular matrix. They recognize extracellular glycoproteins such as fibronectin or vitronectin on the extracellular matrix by means of the RGD sequence occurring in these proteins (RGD is the single letter code for the amino acid sequence arginine-glycine-aspartate).

In general, integrins such as, for example, the vitronectin receptor, which is also called the $\alpha_v\beta_3$ receptor, or alternatively the $\alpha_v\beta_5$ receptor or the GpIIb/IIIa receptor play an important part in biological processes such as cell migration and cell-matrix adhesion and thus in diseases in which these processes are crucial steps. Cancer, osteoporosis, arteriosclerosis, restenosis (reoccurrence of stenosis after percutaneous transluminal angioplasty) and opthalmia may be.mentioned by way of example.

The $\alpha_v\beta_3$ receptor occurs, for example, in large amounts on growing endothelial cells and makes possible their adhesion to an extracellular matrix. Thus the $\alpha_v\beta_3$ receptor plays an important part in angiogenesis, i.e. the formation of new blood vessels, which is a crucial prerequisite for tumor growth and metastasis formation in carcinoses. Furthermore, it is also responsible for the interaction between osteoclasts, i.e. cells resorbing mineralized tissue, and the bone structure. The first step in the degradation of bone tissue consists in the adhesion of osteoclasts to the bone. This cell-matrix interaction takes place via the $\alpha_v\beta_3$ receptor, which is why the corresponding integrin plays an important part in this process. Osteolytic diseases such as osteoporosis are induced by an inequilibrium between bone formation and bone destruction, i.e. the resorption of bone material caused by accumulation of osteoclasts predominates.

It was possible to show that the blockage of the above-mentioned receptors is an important starting point for the treatment of disorders of this type. If the adhesion of growing endothelial cells to an extracellular matrix is suppressed by blocking their appropriate integrin receptors, for example, by a cyclic peptide or a monoclonal antibody, the endothelial cells die. Therefore angiogenesis does not occur, which leads to a cessation or resolution of the tumor growth (cf., for example, Brooks et al., Cell, Volume 79, 1157–1164, 1994).

Moreover, the invasive properties of tumor cells and thus their capability for metastasis formation are markedly decreased if their $\alpha_v\beta_3$ receptor is blocked by an antibody (Brooks et al., J. Clin. Invest., Volume 96, 1815, 1995).

The degradation of bone tissue can be suppressed by blockage of the $\alpha_v\beta_3$ receptors of the osteoclasts, since these are then unable to accumulate on the bone in order to absorb its substance (WO 98/18461, p. 1, 1.24 to p. 2, 1.13).

By means of the blockage of the $\alpha_v\beta_3$ receptor on cells of the smooth aorta vascular musculature with the aid of integrin receptor antagonists, the migration of these cells into the neointima and thus angioplasty leading to arteriosclerosis and restenosis can be suppressed (Brown et al., Cardiovascular Res., Volume 28, 1815, 1994).

In recent years, compounds have therefore been sought which act as antagonists of integrin receptors. For example WO 97/24119 discloses victronectin ($\alpha_v\beta_3$) receptor antagonist as antiosteoporosis agents which are structurally related to the compounds described here, but do not have a broad spectrum of action of this type.

It was the object of the present invention to develop compounds which exhibit a high activity as integrin antagonists and in particular against the $\alpha_v\beta_3$ and/or the $\alpha_v\beta_5$ receptor.

The compounds on which the present invention is based can be described by the following general formula (I):

formula (I)

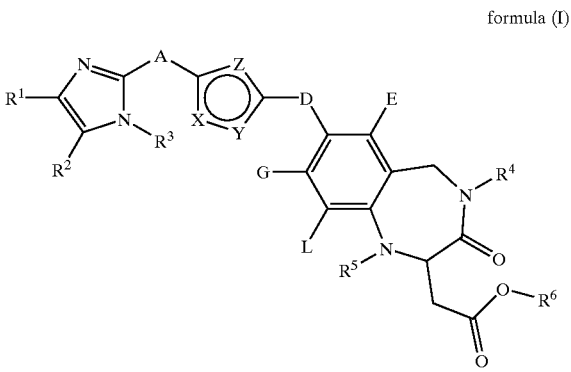

where

R1 and R2 together with the formal double bond bridging them form a phenyl ring or a six-membered aromatic heterocycle having 1 or 2 nitrogen atoms, which is optionally substituted by halogen, nitro, cyano, trifluoromethyl, hydroxyl, ($C_1$–$C_6$)-alkyl, ($C_1$–$C_6$)-alkoxy, ($C_1$–$C_6$)-alkoxycarbonyl, amino, carboxyl, phenoxy, ($C_6$–$C_{10}$)-aryl, ($C_1$–$C_6$)-alkylamino, ($C_1$–$C_6$)-alkylsulfone or a group of the formula —$SO_2NR^aR^b$ wherein $R^a$ and $R^b$ may independently represent hydrogen or ($C_1$–$C_6$)-alkyl, and R3=H or ($C_1$–$C_4$)-alkyl, and A=O, S, ($CH_2$)$_n$ where n=1,2,3 or 4 or N—R7 where R7=H or ($C_1$–$C_4$)-alkyl, or is absent and X, Y, Z=O, S, N, N—R8 where R8=H, ($C_1$–$C_6$)-alkyl or ($C_6$–$C_{10}$)-aryl, or C—(R9)(R10) where R9, R10=H, ($C_1$–$C_6$)-alkyl or ($C_1$–$C_{10}$)-aryl, or C—(R11) if the X, Y or Z in question is participating in a formal double bond, where R11=H, ($C_1$–$C_6$)-alkyl or ($C_6$–$C_{10}$)-aryl, and D=O, S, ($CH_2$)$_n$ where n=1,2,3 or 4, or N—R7 where R7=H or ($C_1$–$C_4$)-alkyl, or is absent and E, G, L=H, halogen, nitro, cyano, trifluoromethyl, hydroxyl, carboxyl, ($C_1$–$C_6$)-alkyl, ($C_1$–$C_6$)-alkoxy or ($C_1$–$C_6$)-alkoxycarbonyl, where E, G and L can be identical or different and R4=H, ($C_3$–$C_8$)-cycloalkyl, ($C_1$–$C_6$)-alkyl, which is optionally substituted by hydroxyl, ($C_1$–$C_6$)-alkoxy or phenyl, where the latter is optionally in turn substituted on the phenyl ring by halogen, ($C_1$–$C_4$)-alkyl, ($C_1$–$C_4$)-alkoxy, hydroxyl, trifluoromethoxy or trifluoromethyl, and R5=H or ($C_1$–$C_4$)-alkyl and R6=H, ($C_1$–$C_6$)-alkyl or benzyl and their salts.

Preferred compounds according to the general formula (I) are those where

R1 and R2 together with the formal double bond bridging them form a phenyl ring or a six-membered aromatic heterocycle having 1 or 2 nitrogen atoms, which is optionally substituted by $(C_1–C_6)$-alkoxy, nitro or amino, and R3=H, and A=O, S, $(CH_2)_n$ where n=1,2,3 or 4 or N—H, or is absent and X, Y, Z=O, S, N, N—R8 where R8=H, $(C_1–C_6)$-alkyl or $(C_6–C_{10})$-aryl, or C—(R9)(R10) where R9, R10=H, $(C_1–C_6)$-alkyl or $(C_6–C_{10})$-aryl, or C—(R11) if the X, Y or Z in question is participating in a formal double bond, where R11=H, $(C_1–C_6)$-alkyl or $(C_6–C_{10})$-aryl, and D=O, S, $(CH_2)_n$ where n=1, 2, 3 or 4, or N—H, or is absent and E, G, L=H, and R4=H, benzyl, cyclopropyl, cyclopentyl, cyclohexyl, phenylethyl or $(C_1–C_4)$-alkyl, which is optionally substituted by hydroxyl or methoxy, and R5=H, and R6=H or methyl.

and their salts.

Particularly preferred compounds according to the general formula (I) are those where R1 and R2 together with the formal double bond bridging them form a phenyl ring, which is optionally substituted by nitro. and R3=H and A=is absent and X=N, Y=O and Z=N or X=N, Y=N and Z=O, S or X=$CH_2$, Y=O, Z=N and D=is absent and E, G, L=H, and R4=methyl, cyclopropyl or $(C_1–C_4)$-alkyl substituted by methoxy and R5=H, and R6=H or methyl and their salts.

The compounds according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention. Those particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The present invention also includes ammonium compounds which can be prepared by conversion of the free amines by means of alkylation.

In the context of the present invention, the substituents in general have the following meaning:

$(C_1–C_6)$-alkyl in general represents, depending on the abovementioned substituents, a straight-chain or branched hydrocarbon radical having 1 to 6, preferably 1 to 4 carbon atoms. Examples which may be mentioned are methyl, ethyl, propyl isopropyl, butyl, isobutyl, pentyl, isopentyl, hexyl, isohexyl.

$(C_1–C_6)$-alkoxycarbonyl can be represented, for example, by the formula

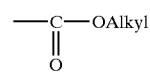

Alkyl here represents a straight-chain or branched hydrocarbon radical having 1 to 6 carbon atoms. Lower alkoxycarbonyl having 1 to 4 carbon atoms in the alkyl moiety is preferred. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

$(C_3–C_8)$-cycloalkyl in general represents a cyclic hydrocarbon radical having 3 to 8 carbon atoms. Cyclopropyl, cyclopentyl and cyclohexyl are preferred. Examples which may be mentioned are cyclopentyl, cyclohexyl, cycloheptyl and cyclooctyl.

$(C_6–C_{10})$-aryl in general represents an aromatic radical having 6 to 10 carbon atoms. Preferred aryl radicals are phenyl and naphthyl.

Halogen in the context of the invention represents fluorine, chlorine, bromine and iodine.

$(C_1–C_6)$-alkoxy in general represents, depending on the abovementioned substituents, a straight-chain or branched hydrocarbon radical bonded via an oxygen atom and having 1 to 6 carbon atoms. Lower alkoxy having 1 to 4 carbon atoms is preferred. An alkoxy radical having 1 to 3 carbon atoms is particularly preferred. Examples which may be mentioned are methoxy, ethoxy, propoxy, isopropoxy, butoxy, isobutoxy, pentoxy, isopentoxy, hexoxy, isohexoxy.

$(C_1–C_6)$-alkylsulfone can be represented by the formula

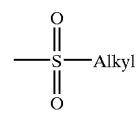

wherein Alkyl represents a straight-chain or branched hydrocarbon radical having 1 to 6, preferably 1 to 4 carbon atoms. Examples which may be mentioned are: methylsulfone, ethylsulfone, propylsulfone, isopropylsulfone.

Six-membered aromatic heterocycles in the context of the invention, depending on the abovementioned substituents, in general represent a 6-membered heterocycle which can contain up to 2 nitrogen atoms and which can optionally also be bonded via a nitrogen atom. Examples which may be mentioned are: pyridyl and pyrimidyl.

In general formula (I) the heterocyclic moiety

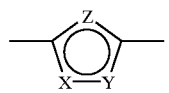

represents an aromatic or partially saturated heterocycle. Preferred examples for this moiety are:

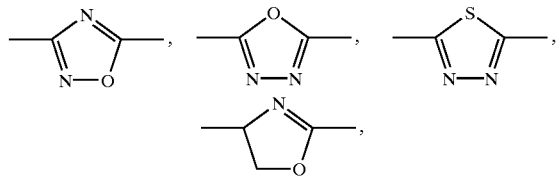

The compounds according to the invention can exist in stereoisomeric forms which either behave as image and mirror image (enantiomers), or which do not behave as image and mirror image (diastereomers). The invention relates both to the enantiomers or diastereomers and their respective mixtures. These mixtures of the enantiomers and diastereomers can be separated into the stereoisomerically uniform constituents in a known manner.

The compounds of the general formula (I) according to the invention can be prepared in the following way using process variant (A) or (B):

(A) reaction of a component (a)

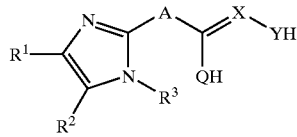

with a component (b)

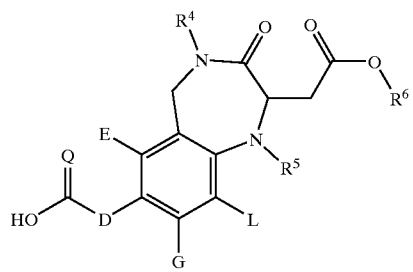

where (b) is first reacted in the presence of sulfonyl chloride, POCl$_3$ or PCl$_5$ to give the acid chloride and is then reacted with (a) in the presence of a base in an inert organic solvent, or a coupling of (a) with (b) is carried out by means of Bis(2-oxo-3-oxazolidinyl) phosphinic chloride (BOP) or carbodiimide reagents, followed by a cyclization reaction which can be effected by means of heat, acids, bases, dehydrating substances and by addition of generally nucleophilic reagents, where, if appropriate, the COOR6 group is finally hydrolyzed and where Q in one of the two components (a) or (b) is oxygen and in the other component corresponds to Z, or (B) reaction of a component (a')

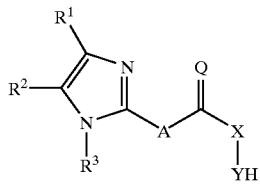

with a component (b)

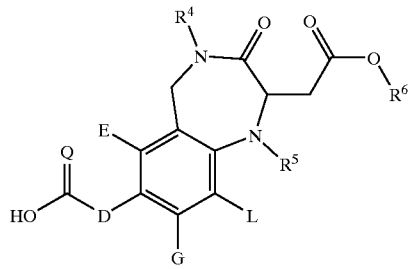

where (b) is first reacted in the presence of sulfonyl chloride, POCl$_3$ or PCl$_5$ to give the acid chloride and then reacted with (a') in the presence of a base in an inert organic solvent, or a coupling of (a') with (b) is carried out by means of BOP or carbodiimide reagents, followed by a cyclization reaction which can be effected by means of heat, acids, bases, dehydrating substances and by addition of generally nucleophilic reagents, where, if appropriate, the COOR6 group is finally hydrolyzed and where Q in one of the two components (a') or (b) is oxygen and in the other component corresponds to Z.

Preferably, in process variant (A), for component (a), X=N, Y=O and Q=NH is employed and for component (b), Q=O is employed and in process variant (B), for component (a'), X=NH, Y=NH and Q=O is employed and, for component (b'), Q=O is employed.

Particularly preferably, it applies to both process variants that R1 and R2 together with the formal double bond bridging them form a phenyl radical,

R3, R5, E, G, L=H,

R4, R6 =methyl and

A, D=is absent.

The compounds of the formula (I) according to the invention have a surprisingly wide spectrum of pharmacological action.

The compounds according to the invention exhibit an antagonistic action against integrin inhibitors, in particular the $\alpha_v\beta_3$ receptor or the $\alpha_v\beta_5$ receptor.

They can be used as active compounds in medicaments for the reduction of changes to vascular walls and are employed for the treatment of arterial hypertension and atherosclerosis. Moreover, they can be employed for the treatment of coronary heart disorders, cardiac insufficiency, disorders of brain function, ischemic brain disorders, (peripheral) circulation disorders, microcirculation disorders and thromboses, functional disorders of the kidney and adrenal gland, bronchospastic and vascular system-related disorders of the airways, sodium retention and edemas as well as osteolytic disorders such as osteoporosis, cancer, carcinoses and ophthalmic diseases.

Furthermore, the proliferation and migration of smooth muscle cells plays a decisive part in the occlusion of vessels.

The compounds according to the invention are suitable for inhibiting this proliferation and can therefore also be employed for the treatment of restenosis.

The novel active compounds are distinguished pharmacologically by good kinetic parameters. In particular, they have favorable properties with respect to clearance.

The novel active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this case the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, if water is used as a diluent organic solvents can optionally be used as auxiliary solvents.

Administration is carried out in a customary manner, preferably orally or parenterally, in particular perlingually or intravenously.

In the case of parenteral administration, solutions of the active compound using suitable liquid carrier materials can be employed.

In general, it has proven advantageous in the case of intravenous administration to administer amounts from approximately 0.001 to 1 mg/kg, preferably approximately 0.01 to 0.5 mg/kg, of body weight to achieve effective results, and in the case of oral administration the dose is approximately 0.01 to 100 mg/kg, preferably 0.1 to 50 mg/kg, of body weight.

In spite of this, if appropriate, it may be necessary to depart from the amounts mentioned, namely depending on the body weight or the type of application route, on individual behavior toward the medicament, the manner of its formulation and the time or interval at which administration takes place. Thus in some cases it may be adequate to manage with less than the abovementioned minimum amount, while in other cases the upper limits mentioned must be exceeded. In the case of the administration of relatively large amounts, it may be advisable to divide these into several individual doses over the course of the day.

The present invention is illustrated in greater detail below by working examples.

Starting Compound I

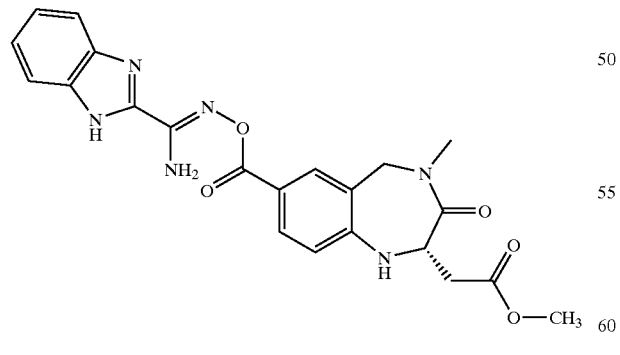

S-O-{(4-Methyl-3-oxo-2,3,4,5-tetrahydro-1H-benzol[e][1,4]diazepine-2-methoxycarbonylmethyl)-7-oyl}benzimidazole-2-carboxamidoxime 0.877 g of methyl S-7-carboxy-2,3,4,5-tetrahydro-4-methyl-3-oxo-1H-1,4-benzodiazepine-2-acetate (Tetrahedron Letters 38, 3131-34, 1997) is stirred under reflux for 1 h with thionyl chloride (40 ml), concentrated and the residue is dissolved in 20 ml of chloroform. The solution obtained is added dropwise to a mixture of 0.53 g of benzimidazole-2-carboxamidoxime (J. Chem. Soc. C, 1967, 28) and chloroform (50 ml), pyridine (0.48 g) and triethylamine (0.30 g). It is stirred at room temperature for 2 h, then concentrated and the residue is taken up in ethyl acetate. After this, washing with water, saturated sodium hydrogencarbonate solution and saturated sodium chloride solution and drying over magnesium sulfate takes place, after concentration an amorphous residue being obtained which is stirred with dichloromethane and filtered off with suction. Recrystallization is carried out from ethanol (0.41 g). The mother liquor is concentrated and chromatographically purified ($CH_2Cl_2$; $CH_2Cl_2/CH_3OH=30/1$). 0.6 g of the title compound is obtained from the mother liquor.

PREPARATION EXAMPLE 1

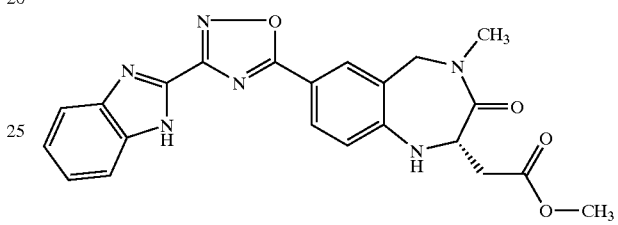

S-Methyl 7-[3-(1H-benzimidazol-2-yl)-[1,2,4]oxadiazol-5-yl]-4-methyl-3-oxo-2,3,4,5-tetrahydro-1H-benzo[e][1,4]diazepine-2-acetate Starting Compound I (900 mg) is dissolved in 20 ml of dimethylformamide and treated with 3 ml of pyridine. The mixture is refluxed for 20 h. It is then treated with water and extracted 3 times with ethyl acetate. Washing with saturated sodium chloride solution and drying over magnesium sulfate yield, after concentration, a residue which is purified by means of flash chromatography (flash chrom. $CH_2Cl_2$; $CH_2Cl_2$/ethyl acetate=1/1; $CH_2/Cl_2$/ethyl acetate/methanol=20/20/1). The fractions are concentrated after TLC and the residue is recrystallized from ethyl acetate/diethyl ether. 256 mg of the title compound are obtained.

PREPARATION EXAMPLE 2

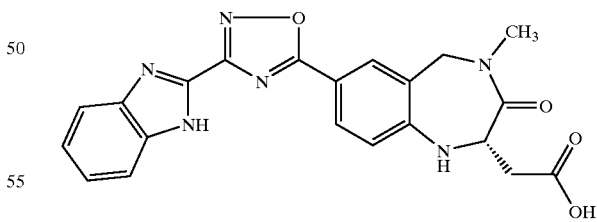

S-{7-[3-(1H-Benzimidazol-2-yl)-[1,2,4]oxadiazol-5-yl]-4-methyl-3-oxo-2,3,4,5-tetrahydro-1H-benzo[e][1,4]diazepin-2-yl}-acetic acid 238 mg of the compound from Preparation Example 1 are dissolved in 10 ml of dimethoxyethane and 8 ml of water. The mixture is then treated with 10 mg of LiOH×$H_2O$ and stirred at room temperature for 2 h. It is extracted twice with ether, the aqueous phase is acidified with acetic acid and the precipitating product is filtered off with suction. The solid is washed with water, dissolved in 150 ml of dichloromethane/methanol/ethanol (1/1/1) and concentrated to 5 ml. The solid obtained is washed with ether (yield: 183 mg). $^1$H NMR (200 MHz, DMSO): 2.59 (1H, dd J=8 Hz), 2.80 (1H, dd, 10 Hz, 17.5 Hz), 2.94 (s, 3H), 4.03 (d, 1H,17.5 Hz), 5.21 (m, 1H), 5.52 (d, 1H, 17.5 Hz), 6.73 (d, 1H, 7.5 Hz), 6.93 (s, 1H), 7.15–7.90 (m, 7H), 13.5 (broad s, 1H).

Starting compound II

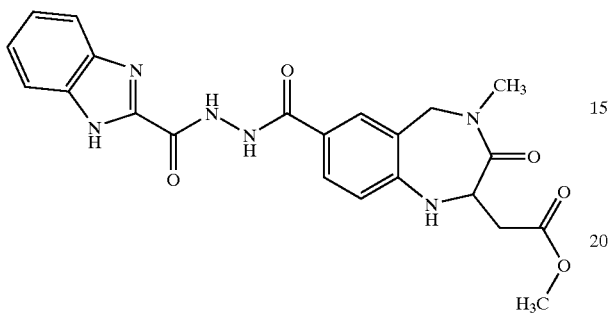

Methyl 7-[N'-(1H-benzimidazole-2-carbonyl)-hydrazinocarbonyl]-4-methyl-3-oxo-2,3,4,5-tetrahydro-1H-benzo[e][1,4]diazepine-2-acetate Methyl 7-carboxy-2,3,4,5-tetrahydro-4-methyl-3-oxo-1H-1,4-benzodiazepine-2-acetate (292 mg) is heated under reflux in 10 ml of thionyl chloride. After this, the mixture is concentrated and the residue is taken up in 10 ml of chloroform. This solution is added dropwise at 0° C. to a mixture of benzimidazole-2-carboxyhydrazide (176 mg), chloroform (30 ml) and pyridine (1 ml). The mixture is stirred for 1 h at 0° C. and for 2 h at room temperature. It is then concentrated again, and the residue is purified by chromatography (CH$_2$Cl$_2$/methanol=20+1). Recrystallization from ethanol yields 194 mg of yellow crystals.

PREPARATION EXAMPLE 3

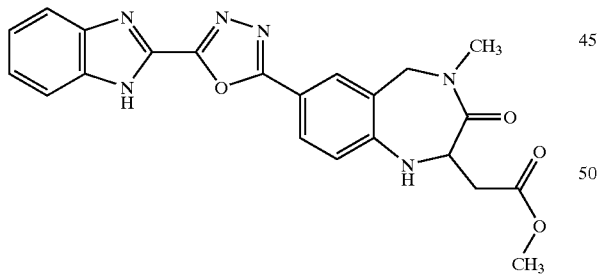

Methyl 7-[5-(1H-benzimidazol-2-yl)-[1,3,4]oxadiazol-2-yl]-4-methyl-3-oxo-2,3,4,5-tetrahydro-1H benzo[e][1,4]diazepine-2-acetate 90 mg of the Starting Compound II are introduced into 15 ml of tetrahydrofuran and treated with 0.2 ml of thionyl chloride. After reflux for 2 h, the mixture is concentrated and the residue is recrystallized from ethanol. The mother liquor is concentrated and purified by chromatography (CH$_2$Cl$_2$/ethyl acetate gradient). The product crystallizes from dichloromethane (yield: 10 mg).

PREPARATION EXAMPLE 4

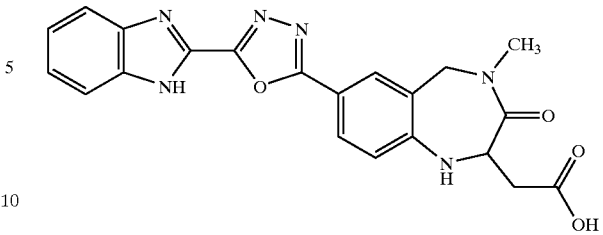

{7-[5-(1H-benzimidazol-2-yl)-[1,3,4]oxadiazol-2-yl]-4-methyl-3-oxo-2,3,4,5-tetrahydro-1H-benzo[e][1,4]diazepin-2-yl}-acetic acid 200 mg of the compound from Preparation Example 3 are treated analogously to Preparation Example 2. 141 mg of the title compound are obtained. $^1$H NMR (200 MHz, DMSO): 2.49 (1H, dd J=5.5 Hz, J=17.5), 2.62 (1H, dd, 8.5 Hz, 17.5 Hz), 2.96 (s, 3H), 3.5 (broad s, 1H), 4.05 (d, 1H, 16.0 Hz), 5.17 (m, 1H), 5.52 (d, 1H, 16.0 Hz), 6.73 (d, 1H, 16.0 Hz), 6.85 (s, 1H), 7.30 (m, 2 H), 7.15–7.70 (m, 5H).

PREPARATION EXAMPLE 5

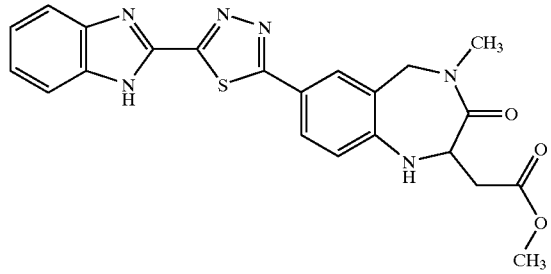

Methyl 7-[5-(1H-benzimidazol-2-yl)-[1,3,4]thiadiazol-2-yl]4-methyl-3-oxo-2,3,4,5-tetrahydro-1H-benzo[e][1,4]diazepine-2-acetate 900 mg of the compound from Starting Compound II are dissolved in 60 ml of THF and treated with 1.2 g of Lawesson's reagent. The mixture is stirred under reflux for 3 h. The crystalline product is filtered off with suction and washed with methylene chloride/diethyl ether (yield: 1.65 g).

An analytical sample is obtained by preparative HPLC. Yellow crystals.

$^1$H NMR (200 MHz, DMSO): 2.67 (1 H, dd J=6 Hz, 17.5 Hz), 2.88 (1H, dd, 10 Hz, 17.5 Hz), 2.96 (s, 3H), 3.62 (s, 3H), 4.07 (d, 1H, 17.5 Hz), 5.22 (m, 1H), 5.51 (d, 1H, 17.5 Hz), 6.65–6.72 (m, 2H), 7.20–7.38 (m, 2H), 7.57 (d, 1H, 7.5 Hz), 7.60–7.80 (m, 3H).

PREPARATION EXAMPLE 6

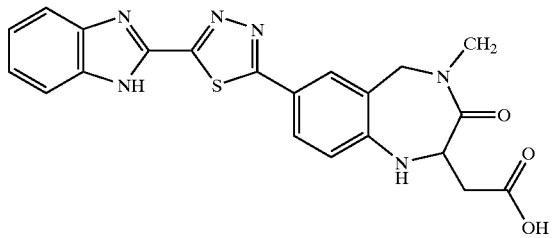

{7-[5-(1H-Benzimidazol-2-yl)-[1,3,4]thiadiazol-2-yl]-4-methyl-3-oxo-2,3,4,5-tertahydro-1H-benzo[e][1,4]diazepin-2-yl }-acetic acid 50 mg of the compound from Preparation Example 5 are treated analogously to Preparation Example 2. 33 mg are obtained as a yellow solid. $^1$H NMR (200 MHz, DMSO): 2.72 (1 H, dd J=7.5 Hz, J=17.5), 2.62 (1H, concealed by water signal), 2.95 (s, 3H), 4.06 (d, 1H, 16.2 Hz), 5.13 (m, 1H), 5.51 (d, 1H, 16.2 Hz), 6.70 (d, 1H, 9 Hz) under: 6.80 (s, broad, 1H), 7.31 (m, 2H), 7.60–7.80 (m, 4H), 13.8 (s, broad, 1H).

Starting Compound III

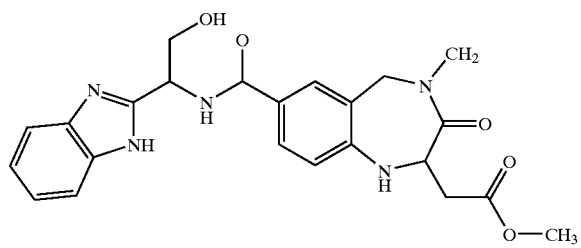

Methyl {7-[1H-(1H-benzimidazol-2-yl)-2-hydroxy-ethylcarbamoyl]-4-methyl-3-oxo-2,3,4,5-tetrahydro-1H-benzo[e][1,4]diazepin-2-yl}-acetate 0.75 g of 2-amino-2-(1H-benzimidazol-2-yl)-ethanol.HCl (Maekawa; Ohtani, Agric. Biol. Chem., 40, 1976, 791) and 0.88 g of methyl 7-carboxy-2,3,4,5-tetrahydro-4-methyl-3-oxo-1H-1,4-benzodiazepine-2-acetate are dissolved in 30 ml of DMF and treated with 0.49 g of 1-hydroxybenzotriazole and 0.58 g of N'-(3-dimethylaminopropyl)-N-ethylcarbodiimide.hydrochloride and 1.55 g of diisopropylethylamine.

The mixture is stirred for 20 h and partitioned between ethyl acetate and water. Extraction 3 times with ethyl acetate and washing of the organic phase with water and saturated sodium chloride solution and subsequent drying over magnesium sulfate and concentration yields a residue which crystallizes using ethyl acetate. 521 mg are obtained from the first crystallizate and 158 mg from the mother liquor.

PREPARATION EXAMPLE 7

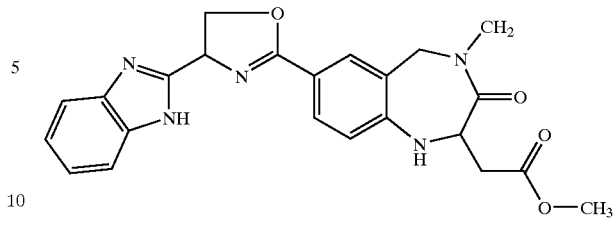

Methyl 7-[4(1H-benzimidazol-2-yl)-4,5-dihydro-oxazol-2-yl]-4-methyl-3-oxo-2,3,4,5-tetrahydro-1H-benzo[e][1,4]diazepine-2-acetate 410 mg of the Starting Compound III are dissolved in 60 ml of tetrahydrofuran and reated with 320 mg of (methoxycarbonylsulfamoyl)-triethylammonium-N-betaine (Burgess reagent). The mixture is heated under reflux for 2 h, concentrated, and partitioned between ethyl acetate and water. Purification on 20 g of silica gel (CH$_2$Cl$_2$/AcOEt/MeOH=40+40+1) leads to 163 mg of gray solid.
$^1$H NMR (200 MHz, CDCl$_3$): 2.68 (dd, 1 H, J=16.0, 6.5) 2.99, 3.10 (each 1 s, 3H) under: 3.0 dd 1H J=16.0, 5.5), 3.66(1H, dd, 17.5 Hz, 9.0 Hz), 3.76 (s, 3H), 4.59 (m, 1H), 4.78–4.99 (m, 2H), 5.11 (m, 1H), 5.29–5.49 (m, 1H), 5.70 (m, 1H), 6.52 (m, 1H), 7.2–7.8 (m, 7H).

PREPARATION EXAMPLE 8

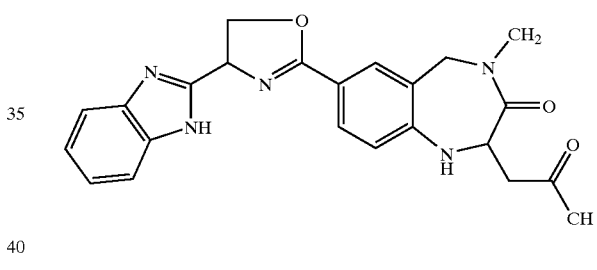

{7-[4-(1H-Benzimidazol-2-yl)-4,5-dihydro-oxazol-2-yl]-4-methyl-3-oxo-2,3,4,5-tetrahydro-1H-benzo[e][1,4]diazepin-2-yl }-acetic acid Analogously to Preparation Example 2, 30 mg of the compound from Preparation Example 7 are dissolved in 5 ml of 1,2-dimethoxyethane and treated with 3 ml of water. 17 mg of slightly reddish crystals are obtained. $^1$H NMR (200 MHz), DMSO): 2.55 (dd, 1H, 5 Hz, 17.5 Hz); 2.79 (dd, 1H, 8.5 Hz, 17.5 Hz); 3.35 (s, 3H), 3.90 (d, 1H, 17.7 Hz), 4.62–4.82 (m, 2H), 5.11 (m, 1H), 5.92–5.61 (m, 2H), 6.47 (d, 1H, 3.75 Hz), 6.61 (d, 1H, 9.5 Hz), 7.15 (m, 2H), 7.42–7.62 (m, 4H), 12.30 (m, 1H), 12.48 (m, 1H).

Starting Compound IV

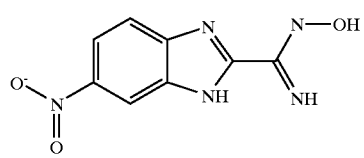

5-Nitro-benzimidazole-2-carboxamide oxime:
(Starting Compound IV)

2 g of 5-nitrobenzimidazole-2-carbonitrile (Lopyrev, V. A.; Larina, L. I.; Baumane, L. Kh.; Shibanova, E. F.; Gavar, R. A.; et al., Chem. Heterocycl. Compd. (Engl. Transl.), EN, 20, 9, 1984, 1021–1026, KGSSAQ, RU, 20, 9, 1984, 1246–1251) are dissolved in 60 ml of ethanol/water (5/1) and treated with 0.74 g of hydroxyl-ammonium chloride and also 1.05 g of sodium acetate and refluxed for 2 h. The mixture is poured into ice water, and the brown precipitate is filtered off with suction and washed with water. 1.6 g of the title compound are obtained.

Starting Compound V

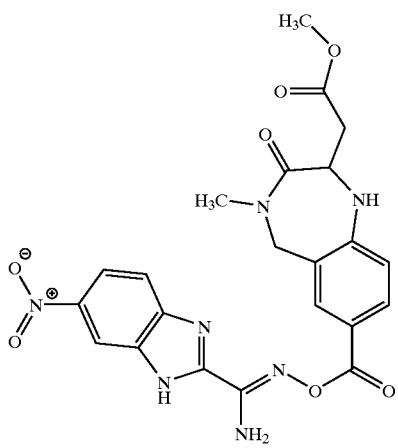

S-O-{(4-Methyl-3-oxo-2,3,4,5-tetrahydro-1H-benzo[e][1,4]diazepine-2-methoxycarbonylmethyl)-7-oyl}-5-nitro-benzimidazole-2-carboxamidoxime 670 mg of 5-nitro-benzimidazol-2-carboxamidoxime are reacted with 880 mg of methyl S-7-carboxy-2,3,4,5-tetrahydro-4-methyl-3-oxo-1H-1,4-benzodiazepine-2-acetate analogously to Starting Compound I. 800 mg of solid are obtained. MS (ESI) 496 (M+H)

PREPARATION EXAMPLE 9

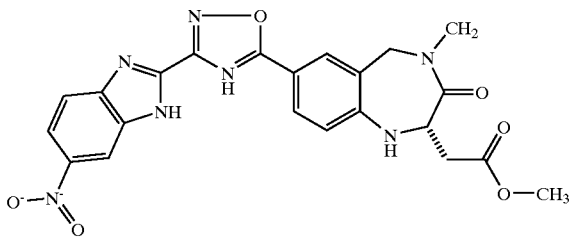

S-Methyl 7-[3-(5-nitro-1H-benzimidazol-2-yl)-[1,2,4]oxadiazol-5-yl]-4-methyl-3-oxo-2,3,4,5-tetrahydro-1H-benzo[e][1,4]diazepine-2-acetate 800 mg of S-O-{(4-methyl-3-oxo-2,3,4,5-tetrahydro-1H-benzo[e][1,4]diazepine-2-methoxycarbonylmethyl)-7-oyl}benzimidazole-2-carboxamidoxime are reacted analogously to Starting Compound II. Colorless solid. MS (ESI): 478 (M+H).

PREPARATION EXAMPLE 10

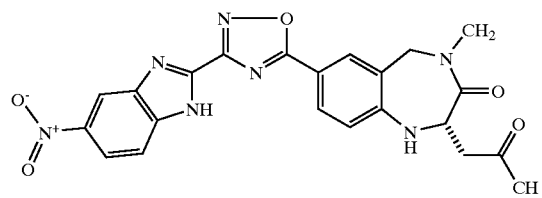

S-7-[3-(5-Nitro-1H-benzimidazol-2-yl)-[1,2,4]oxadiazol-5-yl]-4-methyl-3-oxo-2,3,4,5-tetrahydro-1H-benzo[e][1,4]diazepine-2-acetic acid 40 mg of S-methyl 7-[3-(5-nitro-1H-benzimidazol-2-yl)-[1,2,4]oxadiazol-5-yl]-4-methyl-3-oxo-2,3,4,5-tetrahydro-1H-benzo[e][1,4]diazepine-2-acetate are reacted analogously to Preparation Example 2. 11 mg of yellow solid. $^1$H NMR (400 MHz, DMSO): 2.61 (1 H, dd, J=8 Hz, 18.0 Hz), 2.79 (1H, dd, 10 Hz, 18.0 Hz), 2.96 (s, 3H), 4.03 (d, 1H, 18.0 Hz), 5.22 (m, 1H), 5.53 (d, 1H, 18.0 Hz), 6.75 (d, 1H, 10 Hz), 6.88 (m, 1H), 7.15–8.53 (m, 5H).

Starting Compound VI

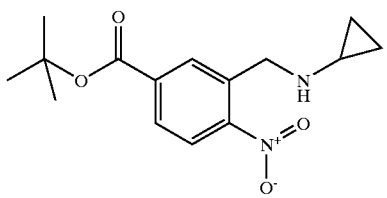

tert-Butyl 3-(cyclopropylamino)methyl-4-nitrobenzoate 23.7 g of tert-butyl 3-(bromomethyl)-4-nitrobenzoate are suspended in 400 ml of EtOH and treated at 0° C. with 9.0 g of cyclopropylamine. The mixture is stirred for 24 h, concentrated, and the residue is crystallized from petroleum ether. The mother liquor is chromatographed and crystallized. 19 g of the title compound are obtained. MS (DCI) 293 (M+H).

Starting Compound VII

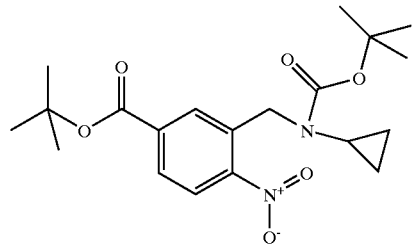

tert-Butyl 3-(N-cyclopropyl-N-tert-butoxycarbonyl)aminomethyl-4-nitrobenzoate 14.8 g of tert-butyl 3-(cyclopropylamino)methyl-4-nitrobenzoate are dissolved in 150 ml of ethyl acetate and treated with 12.1 g of di-tert-butyl dicarbonate. After aqueous working-up and chromatography (petroleum ether/ethyl acetate gradient), 20 g of product are obtained. MS (ESI) 393 (M+H).

Starting Compound VIII

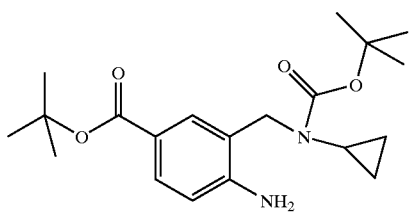

tert-Butyl 3-(N-cyclopropyl-N-tert-butoxycarbonyl)
aminomethyl-4-aminobenzoate 4.9 g of tert-butyl 3-(N-cyclopropyl-N-tert-butoxycarbonyl)aminomethyl-4-nitro-benzoate in 100 ml of ethyl acetate are reduced using 1 g of Pd/C at normal pressure. 4.5 g are obtained as a colorless solid. MS (DCI) 363 (M+H).

Starting Compound IX

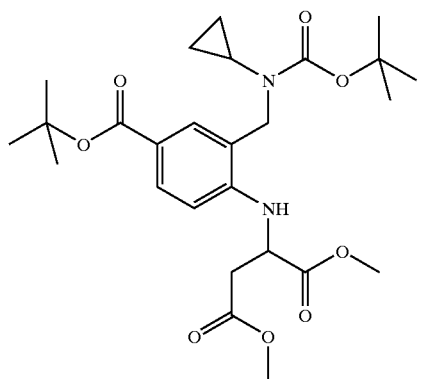

tert-Butyl 4-[2-(1,4-dimethoxy-dioxobutyl)amino]-
3-[[N-3-cyclopropyl-N-tert-butoxycarbonyl)]amino]
methylbenzoate 17.7 g of tert-butyl 3-(N-cyclopropyl-N-tert-butoxycarbonyl)aminomethyl-4-amino-benzoate are heated under reflux with 7.6 g of dimethyl acetylenedicarboxylate in 180 ml of MeOH. After 12 h, the mixture is concentrated, and the material obtained (26 g) is dissolved in methanol/ethyl acetate (1/1) and reduced using 1 g of Pd/C at room temperature at a pressure of 1 bar of hydrogen. Filtering off the catalyst with suction, concentration and chromatography (methylene chloride/ethyl acetate gradient) yield 19 g of the title compound as a colorless oil. MS (ESI) 507 (M+H).

Starting Compound X

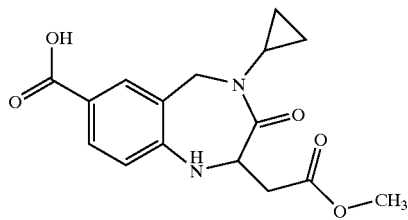

O-{(4-Cyclopropyl-3-oxo-2,3,4,5-tetrahydro-1H-
benzo[e][1,4]diazepine-2-methoxycarbonylmethyl)-
7-oyl}benzimidazole-2-carboxamidoxime 19.1 g of tert-butyl 4-[2-(1,4-dimethoxy-dioxobutyl) amino]-3-[[N-3-cyclopropyl-N-tert -butoxycarbonyl)] amino]methylbenzoate are dissolved in 200 ml of methylene chloride and treated at 0° C. with 80 ml of trifluoroacetic acid. After stirring at room temperature for 12 h, the mixture is concentrated, taken up in 200 ml of MEOH, and treated at −5° with 10.3 ml of trifluoroacetic acid and 65 ml of 30% methanolic sodium methoxide solution. After standing at room temperature for 2 d, the mixture is treated with 6 ml of acetic acid and 80 ml of water with ice-cooling. The precipitation of pale yellow solid is completed by means of half-concentrated hydrochloric acid (to pH 4.5) and it is filtered off with suction. 5.8 g of the title compound are obtained. MS (DCI): 319 (M+H).

Starting Compound XI

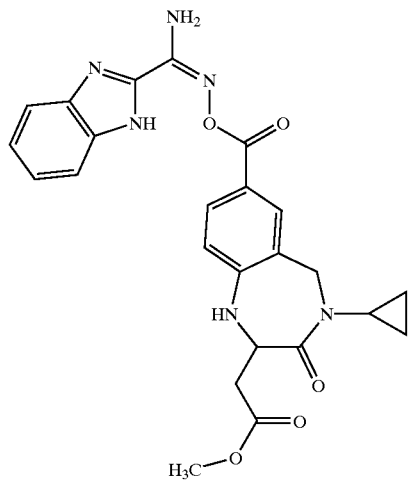

O-{(4-Cyclopropyl-3-oxo-2,3,4,5-tetrahydro-1H-
benzo[e][1,4]diazepine-2-methoxycarbonlmethyl)-7-
oyl}benzimidazole-2-carboxamidoxime Analogously to Starting Compound I, 0.95 g of methyl 7-carboxy-4-cyclopropyl-2,3,4,5 -tetrahydro-3-oxo-1H-1,4-benzodiazepine-2-acetate is reacted with 0.53 g of benzimidazole-2-carboxamide oxime. 0.9 g of the title compound is obtained. MS (ESI): 477 (M+H).

PREPARATION EXAMPLE 11

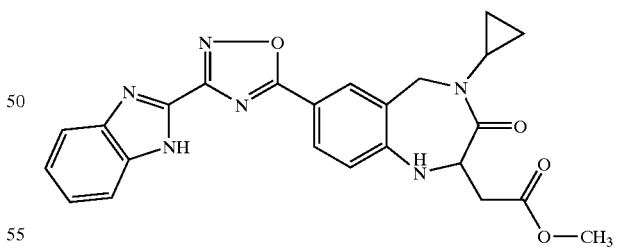

Methyl 7-[3-(1H-benzimidazol-2-yl)-[1,2,4]
oxadiazol-5-yl]-4-cyclopropyl-3-oxo-2,3,4,5-
tetrahydro-1H-benzo[e][1,4]diazepine-2-acetate 900mg of O-{(4-cyclopropyl-3-oxo-2,3,4,5-tetrahydro-1H-benzo[e][1,4]diaze-pine-2-methoxycarbonylmethyl)-7-oyl}benzimidazole-2-carboxamidoxime in 20 ml of DMF and 3 ml of pyridine are heated under reflux (analogously to Example 2). Chromatography (methylene chloride/ethyl acetate/methanol, 40/40/1) and crystallization from methylene chloride/diethyl ether yield 135 mg of yellow crystals. MS (ESI): 459 (M+H).

PREPARATION EXAMPLE 12

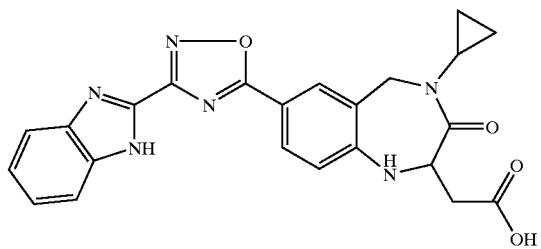

7-[3-(1H-Benzimidazol-2-yl)-[1,2,4]oxadiazol-5-yl] 4-cyclopropyl-3-oxo-2,3,4,5-tetrahydro-1H-benzo[e][1,4]diazepine-2-acetic acid 130 mg of methyl 7-[3-(1H-benzimidazol-2-yl)-[1,2,4]oxadiazol-5-yl]-4-cyclopropyl-3-oxo-2,3,4,5-tetrahydro-1H-benzo[e][1,4]diazepine-2-acetate are hydrolyzed in 4 ml of ethylene glycol dimethyl ether and 3 ml of water and also 90 mg of LiOH analogously to Preparation Example 2. 80 mg are obtained as a colorless solid. $^1$H NMR (400 MHz, DMSO): 0.59 (m, 1H), 0.77 (m, 1H), 2.58 (1 H, dd, J=5.2 Hz, 16.7 Hz) 2.75–2.85 (m, 2H), 2.96 (s, 3H), 4.09 (d, 1H, 16.9 Hz), 5.13 (m, 1H), 5.47 (d, 1H, 16.9 Hz), 6.76 (d, 1H, 8.6 Hz), 6.92 (m, 1H), 7.25–7.90 (m, 6H), 12.5 (broad s, 1H), 13.52 (m, 1H).

PREPARATION EXAMPLE XIII

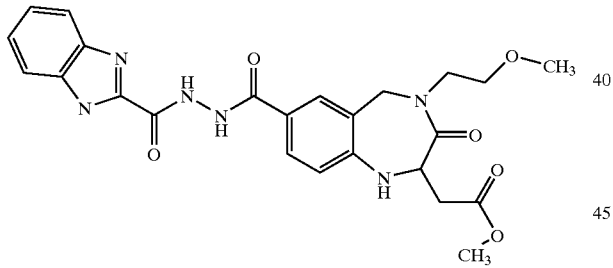

Methyl 7-[N'-(1H-benzimidazole-2-carbonyl)-hydrazinocarbonyl]-4-(2-ethoxy-ethyl)-3-oxo-2,3,4,5-tetrahydro-1H-benzo[e][1,4]diazepine-2-acetate 1130 mg of methyl 7-carboxy-2,3,4,5-tetrahydro-4-(2-methoxyethyl)-3-oxo-1H-1,4-benzodiazepine-2-acetate (1130 mg, preparation analogously to Example 12 using methoxyethylamine) are heated under reflux in 10 ml of thionyl chloride. The mixture is concentrated and the residue is taken up in 50 ml of CHCl$_3$. This solution is added dropwise at 0° C. to a mixture of benzimidazole-2-carboxyhydrazide (510 mg) in CHCl$_3$ (100 ml) and pyridine (2 ml). The mixture is then stirred for 1 h at 0° C. and for 2 h at room temperature. It is then concentrated, and the residue is purified by chromatography (CH$_2$Cl$_2$/MeOH=20+1). Recrystallization from EtOH/AcOEt/Et$_2$O yields 488 mg of yellow crystals. R$_f$=0.25 (CH$_2$Cl$_2$/CH$_3$OH=10:1)

PREPARATION EXAMPLE 13

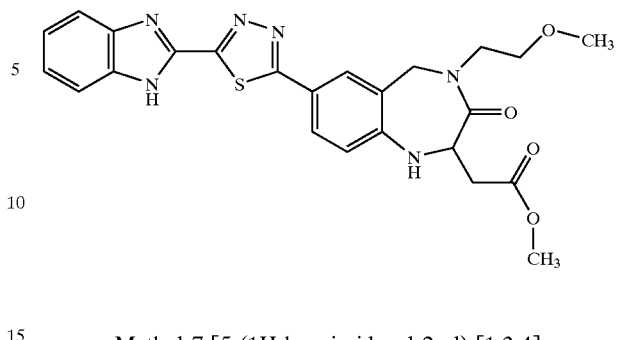

Methyl 7-[5-(1H-benzimidazol-2-yl)-[1,3,4]oxadiazol-5-yl]-4-(2-methoxyethyl)-3-oxo-2,3,4,5-tetrahydro-1H-benzo[e][1,4]diazepine-2-acetate 450 mg of the substance from Example 10 are introduced into 200 ml of THF and treated with 0.8 ml of thionyl chloride. After heating under reflux for 2 h, the mixture is concentrated and the residue is partitioned between AcOEt/NaHCO$_3$ solution. The organic phase is separated off, and washed successively with water and saturated sodium chloride solution. It is dried over MgSO$_4$ and purified by chromatography (CH$_2$Cl$_2$, AcOEt gradient). The product crystallizes from dichloromethane/EtOH (350 mg). R$_f$=0.40 (CH$_2$Cl$_2$/CH$_3$OH=10:1).

PREPARATION EXAMPLE 14

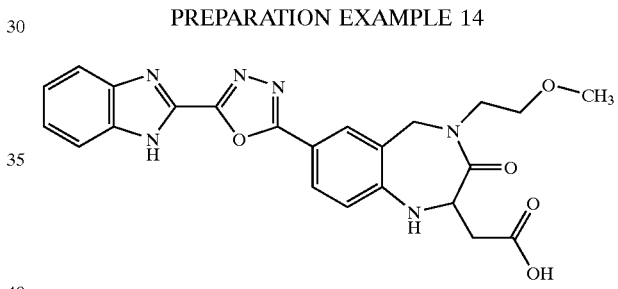

{7-[5-(1H-benzimidazol-2-yl)-[1,3,4]oxadiazol-2-yl]-4-(2-methoxyethyl)-3-oxo-2,3,4,5-tetrahydro-1H-benzo[e][1,4]diazepin-2-yl}-acetate 80 mg of the compound from Example 14 are treated analogously to Preparation Example 3. 63 mg of the title compound are obtained (R$_f$0.42 CH$_2$Cl$_2$/CH$_2$OH=3+1: Example 14: Rf=0.90). $^1$H NMR (200 MHz, DMSO): 2.58 (1H, dd J=5.0 Hz, J=17.0), 2.82 (1H, dd, 9.0 Hz, 17.0 Hz), 3.12 (s, 3H), 3.20–3.70 (m, 5H), 4.18 (d, 1H, 16.0 Hz), 5.20 (m, 1H), 5.51 (d, 1H, 16.0 Hz), 6.69 (s, 1H,) 6.79 (s, 1H), 7.25–7.40 (m, 2H), 7.60–7.84 (m, 4H), 12.4 (br., 1H), 13.8 (br., 1H).

The substances were tested for their ability to inhibit α$_v$β$_3$/echistatin binding analogously to Kumar C. C., Nie H. M., Rogers G. P., Malkowski M., Maxwell E., Catino J. J. and Armstrong L. (Journal of Pharmacology and Experimental Therapeutics 283 (2) (1997) 843–853).

α$_v$β$_3$ Test

α$_v$β$_3$ from human placenta (Smith J. W. and Cheresh, D. A. (1988), *J. Biol. Chem.* 263, 18726–18732) (1 mg/ml 50 mM tris HCl pH 7.4, 100 mM NaCl, 2 mM CaCl$_2$, 1% and octylglucoside) was diluted with test buffer (50 mM tris-HCl pH 7.4, 100 mM NaCl, 1 mM CaCl$_2$, 1 mM MgCl$_2$, 1 mM MnCl$_2$, 0.1% bovine serum albumin) and 55 μl each of this α$_v$β$_3$ solution were added to the wells of a 96-well microtiter plate (about 0.1–0.3 μg of $α_vβ_3$ per well). 2 μl of the substances to be tested dissolved in DMSO were then added. 10 μl (40,000 cpm) of $I^{125}$-echistatin per well were then added and the mixture was incubated for 1 hour at room temperature with careful shaking. It was then treated with 100 μg of wheatgerm-coated yttrium silicate beads (Amersham, type RPNQ0011) in 25 μl of distilled water. After 1 hour at room temperature, the cpm values were measured in a scintillation counter. The $IC_{50}$ values were determined in duplicate from concentration series. The non-specific binding was determined in the presence of 0.1 μM unlabeled echistatin or by addition of 5 mM EDTA to the binding mixture.

What is claimed is:

1. A compound of the formula (I)

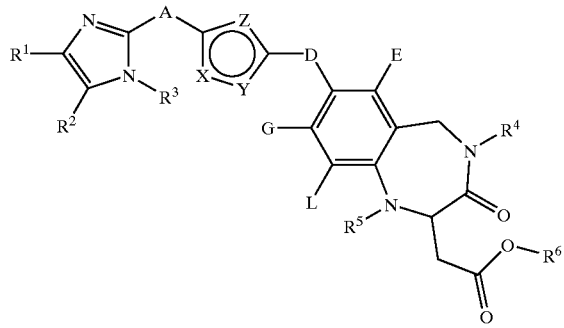

formula (I)

where

R1 and R2 together with the formal double bond bridging them form a phenyl ring or a six-membered aromatic heterocycle having 1 or 2 nitrogen atoms, which is optionally substituted by halogen, nitro, cyano, trifluoromethyl, hydroxyl, ($C_1$–$C_6$)-alkyl, ($C_1$–$C_6$)-alkoxy, ($C_1$–$C_6$)-alkoxycarbonyl, amino, carboxyl, phenoxy, ($C_6$–$C_{10}$)-aryl, ($C_1$–$C_6$)-alkylamino, ($C_1$–$C_6$)-alkylsulfone or a group of the formula —$SO_2NR^aR^b$ wherein $R^a$ and $R^b$ may independently represent hydrogen or ($C_1$–$C_6$)-alkyl, and R3=H or ($C_1$–$C_4$)-alkyl, and A=O,S, $(CH_2)_n$ where n=1,2,3 or 4 or N—R7 where R7=H or ($C_1$–$C_4$)-alkyl, or is absent and X, Y, Z=O, S, N, N—R8 where R8=H, ($C_1$–$C_6$)-alkyl or ($C_6$–$C_{10}$)-aryl, or C—(R9)(R10) where R9, R10=H, ($C_1$–$C_6$)-alkyl or ($C_6$–$C_{10}$)-aryl, or C—(R11) if the X, Y or Z in question is participating in a formal double bond, where R11=H, ($C_1$–$C_6$)-alkyl or ($C_6$–$C_{10}$)-aryl, and D=O, S, $(CH_2)_n$ where n=1,2,3 or 4, or N—R7 where R7=H or ($C_1$–$C_4$)-alkyl, or is absent and E, G, L=H, halogen, nitro, cyano, trifluoromethyl, hydroxyl, carboxyl, ($C_1$–$C_6$)-alkyl, ($C_1$–$C_6$)-alkoxy or ($C_1$–$C_6$)-alkoxycarbonyl, where E, G and L can be identical or different and R4=H, ($C_3$–$C_8$)-cycloalkyl, ($C_1$–$C_6$)-alkyl, which is optionally substituted by hydroxyl, ($C_1$–$C_6$)-alkoxy or phenyl, where the latter is optionally in turn substituted on the phenyl ring by halogen, ($C_1$–$C_4$)-alkyl, ($C_1$–$C_4$)-alkoxy, hydroxyl, trifluoromethoxy or trifluoromethyl, and R5=H or ($C_1$–$C_4$)-alkyl and R6=H, ($C_1$–$C_6$)-alkyl or benzyl, or a pharmaceutically acceptable salt thereof.

2. A compound of the formula (I) as claimed in claim 1, wherein

R1 and R2 together with the formal double bond bridging them form a phenyl ring or a six-membered aromatic heterocycle having 1 or 2 nitrogen atoms, which is optionally substituted by ($C_1$–$C_6$)-alkoxy, nitro or amino, and R3=H, and A=O, S, $(CH_2)_n$ where n=1,2,3 or 4 or N—H, or is absent and X, Y, Z=O, S, N, N—R8 where R8=H, ($C_1$–$C_6$)-alkyl or ($C_6$–$C_{10}$)-aryl, or C—(R9)(R10) where R9, R10=H, ($C_1$–$C_6$)-alkyl or ($C_6$–$C_{10}$)-aryl, or C—(R11) if the X, Y or Z in question is participating in a formal double bond, where R11=H, ($C_1$–$C_6$)-alkyl or ($C_6$–$C_{10}$)-aryl, and D=O, S, $(CH_2)_n$ where n=1, 2, 3 or 4, or N—H, or is absent and E, G, L=H, and R4=H, benzyl, cyclopropyl, cyclopentyl, cyclohexyl, phenylethyl or ($C_1$–$C_4$)-alkyl, which is optionally substituted by hydroxyl or methoxy, and R5=H, and R6=H or methyl, or a pharmaceutically acceptable salt thereof.

3. The compound of formula (I) according to claim 1, wherein

R1 and R2 together with the formal double bond bridging them form a phenyl ring, which is optionally substituted by nitro and R3=H and A=is absent and X=N, Y=O and Z=N or X=N, Y=N and Z=O, S or X=$CH_2$, Y=O, Z=N, and D=is absent and E, G, L=H, and R4=methyl, cyclopropyl or (C1–C4)-alkyl substituted by methoxy and R5=H, and R6=H or methyl, or a pharmaceutically acceptable salt thereof.

4. A method of treating osteoporosis, carinoses, and/or atherosclerosis in a mammal, comprising administering to said mammal an effective amount of a compound according to claim 1.

5. A pharmaceutical composition comprising one or more compounds of the formula (I) as claimed in claim 1 and a pharmaceutical auxiliary.

* * * * *